(12) United States Patent
Balasubramaniam et al.

(10) Patent No.: US 9,261,486 B2
(45) Date of Patent: Feb. 16, 2016

(54) TECHNIQUE FOR IMAGING USING ARRAY OF FOCUSED VIRTUAL SOURCES USING PHASED EXCITATION

(75) Inventors: Krishnan Balasubramaniam, Chennai (IN); Saivathan Alavudeen, Chennai (IN); Chitti Venkatta Krishnamurthy, Chennai (IN)

(73) Assignee: INDIAN INSTITUTE OF TECHNOLOGY, Chennai, State of Tamil Nadu (IN)

( * ) Notice: Subject to any disclaimer, the term of this patent is extended or adjusted under 35 U.S.C. 154(b) by 407 days.

(21) Appl. No.: 13/575,231

(22) PCT Filed: Jan. 28, 2011

(86) PCT No.: PCT/IN2011/000058
§ 371 (c)(1),
(2), (4) Date: Jul. 25, 2012

(87) PCT Pub. No.: WO2011/092718
PCT Pub. Date: Aug. 4, 2011

(65) Prior Publication Data
US 2012/0291553 A1   Nov. 22, 2012

(30) Foreign Application Priority Data

Jan. 28, 2010   (IN) .............................. 214CHE/2010

(51) Int. Cl.
*G01N 29/06*   (2006.01)
*G01N 29/26*   (2006.01)
*G01S 7/52*   (2006.01)
(Continued)

(52) U.S. Cl.
CPC ............ *G01N 29/069* (2013.01); *G01N 29/262* (2013.01); *G01S 7/5209* (2013.01); *G01S 7/52036* (2013.01); *G01S 15/8915* (2013.01); *G01S 15/8927* (2013.01); *G01S 13/90* (2013.01); *G01S 13/9035* (2013.01); *G01S 15/8997* (2013.01); *G01S 17/89* (2013.01); *G01S 17/895* (2013.01)

(58) Field of Classification Search
CPC ... G01N 29/26; G01N 29/069; G01N 29/262; G01N 21/88
USPC ........... 73/597–600, 602, 618, 620, 625, 627, 73/628
See application file for complete search history.

(56) References Cited

U.S. PATENT DOCUMENTS 5,229,933 A * 7/1993 Larson, III ..................... 600/459
5,897,501 A * 4/1999 Wildes et al. .................. 600/447
(Continued)

OTHER PUBLICATIONS

Botros Y.Y. et al., "Two-step hybrid virtual array ray (VAR) technique for focusing through the rib cage", IEEE Transactions on Ultrasonics, Ferroelectrics and Frequency Control IEEE USA, vol. 45, No. 4, Jul. 1998, pp. 989-1000, XP002633789.

*Primary Examiner* — Helen Kwok
(74) *Attorney, Agent, or Firm* — Maschoff Brennan, PLLC (57) ABSTRACT

The invention relates to a method and a device for detecting, measuring and evaluating defects in an object and/or specific material property of an object using a phased array wave technique. The device comprises of a phased array transceiver probe/source and control unit for use in a phased array wave technique for transmitting and receiving wave signals on and from the area to be inspected. The phased array source is divided into a plurality of virtual probes/sources and each virtual probe/source comprises of plurality of elements arranged sequentially but without phasing for excitation.

20 Claims, 5 Drawing Sheets

(51) Int. Cl.
*G01S 15/89* (2006.01)
*G01S 13/90* (2006.01)
*G01S 17/89* (2006.01)

(56) References Cited

U.S. PATENT DOCUMENTS

| | | | |
|---|---|---|---|
| 6,111,816 A * | 8/2000 | Chiang et al. | 367/7 |
| 6,582,367 B1 * | 6/2003 | Robinson et al. | 600/443 |
| 6,868,729 B2 * | 3/2005 | Amemiya | 73/626 |
| 7,322,936 B2 * | 1/2008 | Takeuchi | 600/447 |
| 7,412,890 B1 * | 8/2008 | Johnson | G21C 17/007 73/618 |
| 7,517,317 B2 * | 4/2009 | Lazenby et al. | 600/459 |
| 7,650,789 B2 * | 1/2010 | Portzgen | G01N 29/07 600/447 |
| 7,752,913 B2 * | 7/2010 | Heckel | G01N 29/069 73/584 |
| 7,927,280 B2 * | 4/2011 | Davidsen | 600/447 |
| 8,429,972 B2 * | 4/2013 | Karasawa | G01S 7/52085 702/39 |
| 8,490,490 B2 * | 7/2013 | Yamano | 73/602 |
| 8,701,492 B2 * | 4/2014 | Mizota et al. | 73/603 |
| 8,845,540 B2 * | 9/2014 | Tsao et al. | 600/447 |
| 2002/0111568 A1 | 8/2002 | Bukshpan | |
| 2003/0236461 A1 * | 12/2003 | Poland | G01N 29/0609 600/443 |
| 2004/0267135 A1 | 12/2004 | Takeuchi | |
| 2005/0081636 A1 * | 4/2005 | Barshinger et al. | 73/606 |
| 2005/0183505 A1 * | 8/2005 | Kono et al. | 73/597 |
| 2006/0219013 A1 * | 10/2006 | Baba et al. | 73/618 |
| 2006/0241429 A1 * | 10/2006 | Ustuner | G10K 11/346 600/437 |
| 2008/0110266 A1 * | 5/2008 | Randall et al. | 73/661 |
| 2008/0134791 A1 * | 6/2008 | Schulz et al. | G01N 29/07 73/625 |
| 2008/0190205 A1 * | 8/2008 | Messer et al. | 73/592 |
| 2009/0048789 A1 * | 2/2009 | Yu | G01N 29/069 702/39 |
| 2009/0178484 A1 * | 7/2009 | Kroning et al. | 73/598 |
| 2009/0234230 A1 * | 9/2009 | Bercoff | G01S 7/52049 600/447 |
| 2009/0293621 A1 * | 12/2009 | Kitazawa et al. | 73/606 |
| 2010/0217544 A1 * | 8/2010 | Yan et al. | 702/56 |
| 2010/0242613 A1 * | 9/2010 | Simard et al. | 73/641 |
| 2012/0036934 A1 * | 2/2012 | Kroning et al. | 73/628 |

\* cited by examiner

TECHNIQUE FOR IMAGING USING ARRAY OF FOCUSED VIRTUAL SOURCES USING PHASED EXCITATION

FIELD OF THE INVENTION

The invention relates to a method and device for indentifying and evaluating defects including anomalies in an object or a media, particularly the invention uses a phased array wave technique for inspecting objects including media.

BACKGROUND OF THE INVENTION

Phased array has emerged as a rapid imaging technique in bio-medical and non-destructive evaluation applications, where ultrasonic waves are used for imaging. Other applications in the field of Radar imaging, Ground penetrating Radar (GPR) imaging, etc. can be found where microwaves are employed for imaging. This phased array method is preferred over conventional single transducer method is due to its flexibility in varying the angle of interrogation and/or focusing of the wave field to the point of interest through electronic means reducing the need to move the probe physically and at the same time increasing the imaging volume.

Since the phased array is based on the superposition of waves, the depth to which inspection is possible is directly related to the aperture size (and consequently the near field) of the phased array transducer. In the case of interrogation of thick materials, this limitation is a handicap. Increasing the number of active elements of the phased array system significantly adds additional complexity and cost in the electronic part of the system.

Other deficiencies of the current phased array focusing methods are (a) the focusing quality decreases with increase in the angle of orientation of the beam, (b) in case of complex geometries, there is no provision for any optimisation based on the geometries, (c) the current imaging uses only longitudinal ultrasonic waves in the case of imaging using ultrasonics in materials (d) the current phased array imaging techniques have limited compensation for material anisotropy and inhomogenity, (e) the current phased array imaging methods have limited applications when the surface contours of the material being interrogated is non-uniform.

OBJECT OF THE INVENTION

The first object of the present invention is to identify and evaluate a defect/anomaly in an object/media with improved resolution.

The second object of the invention is to identify and evaluate specific material properties of an object/media with improved resolution and reduced apriori information.

SUMMARY OF THE INVENTION

The invention relates to a method and device for identification and evaluation of defects/anomalies in an object/media. The device includes a phased array transceiver probe and a control unit, and the device is operated with a phased array wave technique for transmitting and receiving wave signals on and from the area to be inspected. The device contains a virtual probes, the probes secondly referred to as virtual sources in this specification, each virtual probe/source includes elements arranged sequentially but without phasing for excitation. Each element of the virtual probe/source receives one pulse and the elements together creates plurality of beams having same phase and amplitude, thereby creating a single virtual beam having a specific angle and focused at a specific depth. The control unit controls the transmission and reception of the phased array probe/source such that a the virtual probes/sources, each probe/source transmits and receives wave signals directly onto and from the area of the object to be inspected. The control unit directs a wave signals onto the area to be inspected, and evaluates the defect/anomaly by manipulation of measured signals of the plurality of virtual probes/sources. The device provides facility to focus anywhere in the area to be inspected. It is to be understand either all, some or at least one virtual probe/source may be as described above to form the device.

Furthermore, the invention also discloses a method of using a phased array trans-receiver probe/source and control unit and identifying the defects/anomalies and evaluating the defects/anomalies in an object/media and/or for identifying and evaluating specific material property of the object/media using phased array wave technique.

DESCRIPTION OF THE DRAWINGS

| S. NO | PART NAME | PART NO |
|---|---|---|
| 1. | Virtual source | 1 |
| 2. | Focal depth | 2 |
| 3. | Aperture size | 3 |
| 4. | Transducer elements | 4 |
| 5. | Phased Array | 5 |
| 6. | 135 mm | 6 |
| 7. | Cross axis width | 7 |
| 8. | Streak | A, B & C |
| 9. | streak from the notch corner | D |
| 10. | Crack length | E |

Few embodiments of the methods according to the invention for determining defects/anomalies in objects/media, and of the device according to the invention is explained with reference to few figures illustrated herein.

In the drawings annexed.

DETAILED DESCRIPTION OF THE INVENTION

The present invention relates to a defect/anomaly identification device for identifying and evaluating defects/anomalies in an object/media and also specific material properties of the object/media. The device includes a phased array transceiver probe referred alternatively as probe/source, each meaning the same as the other, and the device is operated with a phased array wave technique for transmitting and receiving wave signals on and from the area to be inspected. The device contains a plurality of virtual probes/sources, each virtual probe/source includes plurality of elements arranged sequentially but without phasing for excitation. Each element of the virtual probe/source receives one pulse and the plurality of elements together creates plurality of beams having same phase and amplitude, thereby creating a single virtual beam having a specific angle and focused at a specific depth. The device includes a control unit which controls the phased array probe/source such that a plurality of the virtual probes/sources, each probe/source transmits and receives an wave signals directly onto and from the area of the object to be inspected. The control unit directs a plurality of wave signals onto the area to be inspected, and evaluates the defect/anomaly by manipulation of measured signals of the plurality of virtual probe/sources. The other embodiments have all, some or just one characterised novel probe/source as described above.

The invention also discloses a method for detecting defects/anomalies, measuring and evaluating defects/anomalies in an object/media and/or specific material property of an object using a phased array wave technique, which involves the following steps of dividing a phased array trans-receiver probe/source into a plurality of virtual probes/sources and arranging plurality of elements in each virtual probe/source sequentially but without phasing for excitation. Further, allowing each element in the virtual probe/source to receive one pulse and plurality of elements together creating a plurality of beams having same phase and amplitude thereby virtually creating a single beam having a specific angle and focused at a specific depth. Allowing the control unit to transmit and receive the wave signals via plurality of virtual probes/sources in a controlled manner onto an area to be inspected. Evaluating with the control unit the defect/anomaly and/or specific material property on the inspected area by manipulation of measured signals of the plurality of virtual probes/sources. The invention offers a simple but reliable inspection of objects with improved device and improved method.

Figure 1:
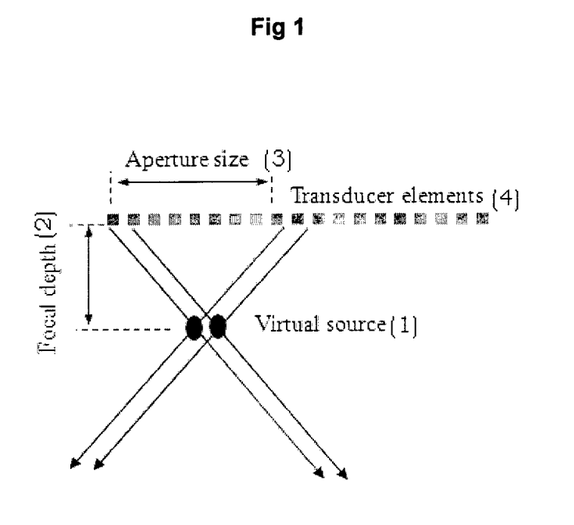
FIG. 1 illustrates the virtual source created by a phased array.

Typical Implementation of the Technique for Imaging Using Array of Focused Virtual Sources (TIVAS) Described Herein for Better Understanding of the Invention In this section, application of TIVAS for non destructive testing (NDT) of thick components with crack is discussed. The surface cracks were formed by conducting fatigue fracture test on a mild steel cruciform specimen of 135 mm thickness. TIVAS employs virtual point sources (Frazier and O'Brien, 1998) generated in the medium using phased array focusing, exploits the electronic scan option of the phased array system and takes advantage of Synthetic Aperture Focused Technique (SAFT) algorithms to provide imaging capabilities at greater depths. TIVAS is similar to the single element scanning technique where the individual elements of a phased array probe/source are excited, without any phasing, in a sequential manner from one end of the probe/source head to another, and the focusing is achieved using the Synthetic Aperture Focused Technique (SAFT) algorithm (Satyanarayanan et al., 2009). One of the main drawbacks encountered in imaging defects/anomalies using single element scanning method is that a single element generates less energy due to its small size, resulting in a poor signal to noise ratio (SNR) which limits the depth of interrogation. This drawback is overcome with TIVAS as it operates with focal spots as virtual point sources. Virtual sources are high intensity sources (due to focusing and due to the use of several elements of the probe/source during excitation) and enables inspection of deeper regions with improved SNR. As the electronic scanning option of the phased array system can be used to perform scans with virtual sources (FIG. 1). The FIG. 1 illustrates the virtual source created by a phased array. In the FIG. 1 numeral 1 is 'virtual source', numeral 2 is 'Focal depth', numeral 3 is 'Aperture size', and numeral 4 is 'Transducer elements' and as the virtual sources are small enough to be considered as "point" sources, SAFT operations can be carried out with TIVAS leading to good lateral resolution capabilities at greater depths. It is well known that the focal depth is depending on the near field (Fresnel zone) of the transducer and the near field depth of a probe/source is related to the square of the aperture dimension. Hence, by using a set of virtual sources that have a significantly higher aperture (using the electronic scanning of an array probe/source), the focal depth can be increased significantly. Reconstruction using the Synthetic Aperture Focusing Technique (SAFT) algorithm was carried out with virtual sources located at a depth equal to the focal depth. A further advantage with TIVAS is that it offers a scan step smaller than the pitch unlike the single element scanning technique where the scan step is limited to the pitch of the probe/source.

Figure 2:
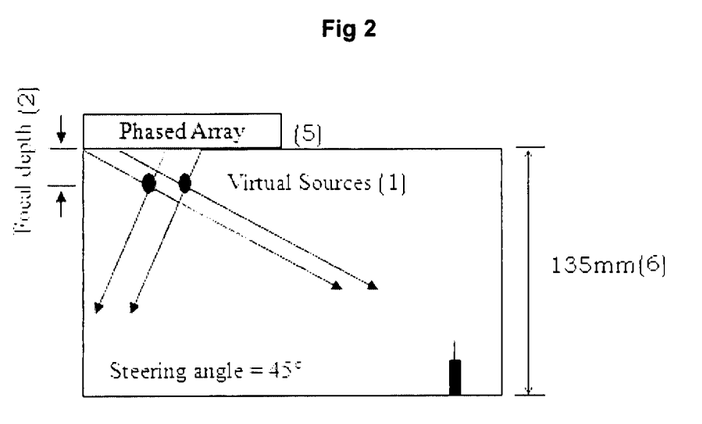
FIG. 2 illustrates "Inspection of Fracture crack in configuration II using Technique for imaging using array of focused virtual sources(TIVAS).

Inspection of Fracture Crack in Thick Cruciform Sample from Bottom Side Using TIVAS is Described Herein An ultrasonic phased array system and a 128 element linear phased array probe/source operating at 5 MHz frequency have been used for carrying out the experiments to assess the notch and crack depth profiles. The beam was steered at an angle of 45° for better probability of detection of vertical crack (FIG. 2). FIG. 2 illustrates "Inspection of Fracture crack in configuration II using TIVAS. In FIG. 2, numeral 1 is 'Virtual Source', numeral 2 is 'Focal depth', numeral 5 is 'Phased array', numeral 6 is "135 mm" Since phased array provides facility to focus anywhere in the medium, a detailed study on focusing behaviour of phased array was conducted to decide the focal depth.

Simulation Studies on Focusing Behaviour of Phased Arrays

Figure 3:
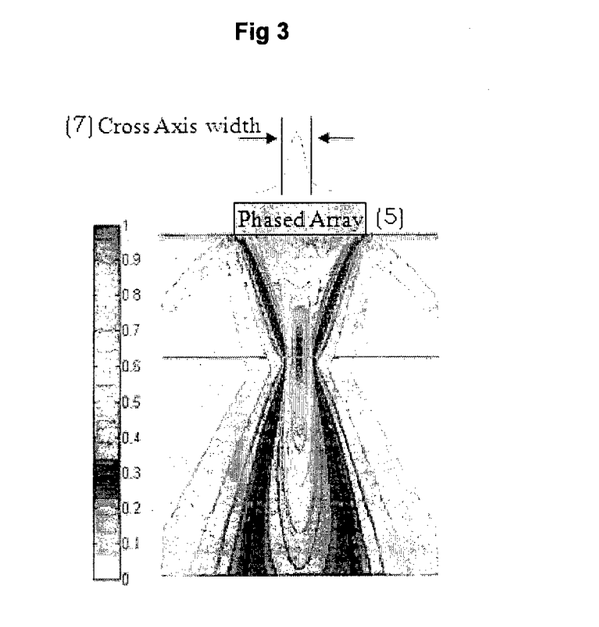
FIG. 3 illustrates "Intensity variation when a 16 element 5 MHz phased array probe/source focused at 10 mm and steered at 0° in Aluminum.

In SAFT reconstruction technique, the lateral resolution of the reconstructed image is a function of width of the source (Cutrona, 1975). Since TIVAS also employs SAFT reconstruction technique and the virtual point sources are generated by phased array focusing, it is important to study the focusing behavior of phased arrays. The Finite difference time-domain (FDTD) based simulation was extended to study the phased array beam formation, and the result was compared with the analytical result. The resultant velocity at each node in the entire computation domain was recorded in a data file at each time step of the simulation time span and the maximum velocity occurring at each node was also stored separately. A 2D intensity plot of the computational domain was generated by assigning this value to the corresponding node (FIG. 3). FIG. 3 illustrates " Intensity variation when a 16 element 5 MHz phased array probe/source focused at 10 mm and steered at 0° in Aluminum. In FIG. 3 numeral 5 is 'Phased array' and numeral 7 is 'Cross Axis width'. The 6 dB width of the cross axis plot on the focal plane was taken as focal spot size. Focal spot sizes of beams generated by 16 elements steering at 45° and focusing at various depths at an interval of 2 mm were estimated. Since focal spot corresponding to 2 mm was outside the half power beam width of few elements, it was not considered.

Apart from the FDTD simulation tool, a semi analytic model was also used to study focal spot size variation with focal depth of a phased array transducer. The semi analytical model is based on the expression developed by Miller and Pursey (Miller and Pursey, 1954). The displacement at any point in the medium due to a transducer of a small but finite width placed on free surface is calculated from the expression $$u_R \sim \frac{ae^{i(\frac{3}{4}\pi - R)}}{c_{44}} \sqrt{\frac{2}{\pi R}} \frac{\cos\theta(\mu^2 - 2\sin^2\theta)}{F_0(\sin\theta)} \quad (6)$$

where $\mu_R$ is the radial component of the displacement due to the transducer of width 'a', $$\mu = \sqrt{\frac{C_{11}}{C_{44}}},$$

$C_{11}$ and C44 are material constants. The function $F_n$ is defined as $$F_0(\zeta) = (2\zeta^2 - \mu^2)^2 - 4\zeta^2\sqrt{(\zeta^2 - 1)(\zeta^2 - \mu^2)} \quad ((7)$$

Particle displacement due to the ultrasonic field from each element was calculated using expressions (6-7) and summed up to get the displacement distribution when a phased beam is focused at any depth. The time delays between individuals are implemented by employing equivalent phase delays for all the individual elements.

Figure 4:
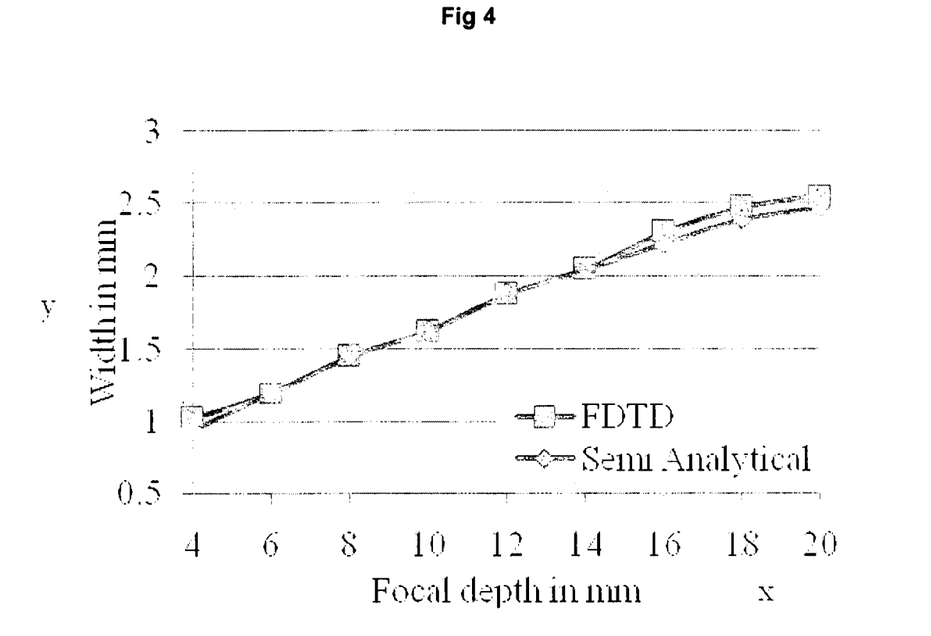
FIG. 4 illustrates 'Focal spot size variation with respect to focal depth in steel for a 16 element 5 MHz phased array probe/source'. The x-axis is marked as focal depth in mm and y-axis marked as width in mm.

The focal spot size of the focused beam at various focal depths in a steel sample was calculated using both FDTD and semi-analytical method. The estimations of two methods were in good agreement (FIG. 4). FIG. 4 illustrates 'Focal spot size variation with respect to focal depth in steel for a 16 element 5 MHz phased array probe/source'. The x-axis is marked as focal depth in mm and y-axis marked as width in mm. Based on the simulation study, focal depth of 4 mm was chosen for TIVAS inspection of cruciform sample in configuration II.

Result of TIVAS Inspection in Thick Cruciform Sample

The simulation of TIVAS inspection in thick cruciform sample was carried out by modeling the 135 mm thick sample with starter notch and fracture crack. The phased array probe/source was placed on the opposite side (bottom of the cruciform sample) of the crack. 16 elements were excited at predetermined time delay to generate ultrasonic beam steering at an angle of 45° and focusing at a depth of 4 mm. SAFT algorithm was carried out on the B-scan data and the image of fracture crack with improved resolution was reconstructed. The SAFT was performed by assuming the sources were located inside the medium a depth of 4 mm and its excitation was at 45° to the normal.

Figure 5:
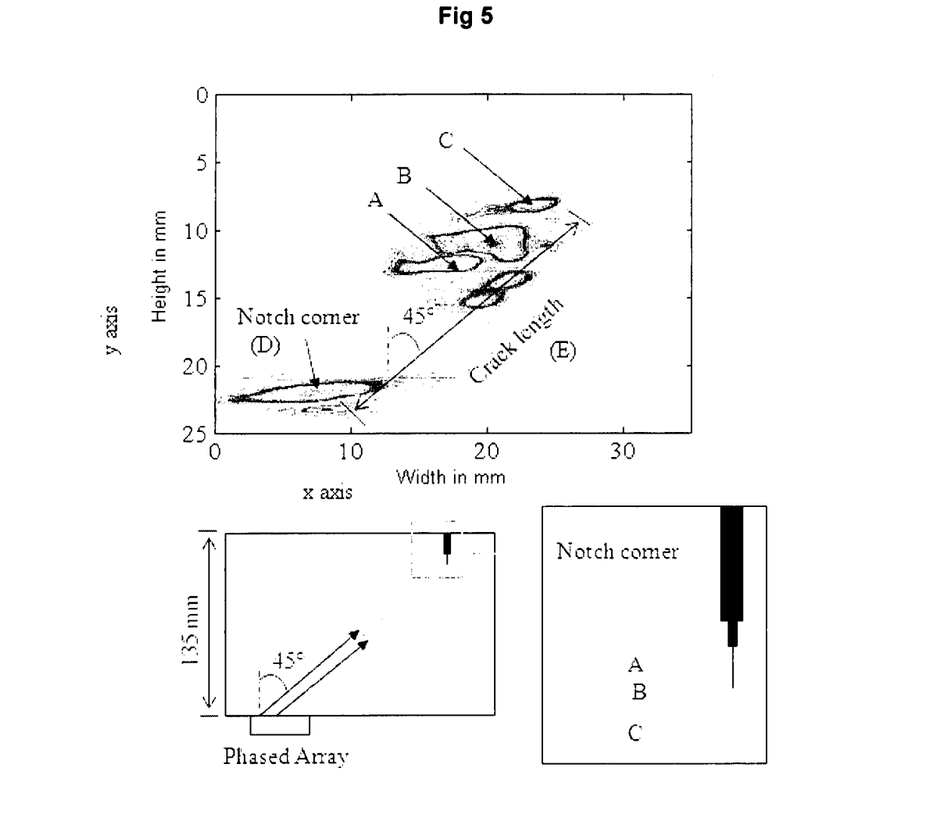
FIG. 5 illustrates 'Simulated result of TIVAS inspection of fracture crack in configuration II'. (width in mm is marked along x-axis and height in mm is marked along the y-axis.)

The reconstructed image is shown in FIG. 5. FIG. 5 illustrates 'Simulated result of TIVAS inspection of fracture crack in configuration II'. In figure width in mm is marked along x-axis and height in mm is marked along the y-axis. Apart from the three streaks (A, B and C), another streak from the notch corner(D) is present in configuration II B-scan image. Since the corner is the one end of the crack, distance between notch streak and fracture crack streak gives the sizing of crack (crack length E). Similarly, dimensions of starter notch also may be calculated from the reconstructed image.

There are many advantages which are useful in the working of the invention and there are also many advantages in making the invention. Some of these are detailed below.

The novel method proposed in the invention will allow for improved imaging using an array of focused virtual sources that are generated using a phased excitation of transducer elements in a multi-element array.

In the invention, the focused virtual sources act as near-point sources of excitation inside the volume of the material being interrogated (imaged).

The invention exhibits the advantage which is that the physical location of these virtual focused sources can be very different from the physical location of the transducer elements that are generating these focused virtual sources.

Further as per the invention, the configurations of these virtual focused sources can be very different from the configurations of the transducer elements that are generating these focused virtual sources.

The invention exhibits a feature such that the angle of the focusing that leads to the generation of the focused virtual source can be tuned to the final geometry of the volume to be imaged.

Furthermore in the manner designed of the configuration, the configurations of the virtual focused sources can be optimised to image a specific geometry of the imaging volume and the configurations of the virtual focused sources can be optimised to image a specific materials property associated with the imaging volume.

As envisaged in the invention the configurations of the virtual focused sources can be 2 Dimensional or 3 Dimensional within the imaging volume.

As described above, the wave technique can use different modes of waves (longitudinal, transverse, and guided (Rayleigh, Lamb, cylindrical, circumferential, axial, flexural, SH, SV)), can be used for either individually imaging or simultaneously imaging using focused virtual sources and will depend on the material properties and the geometry of the imaging volume.

Since, the technique is wave technique, the image reconstruction techniques can utilize any algorithm that uses the phase of the wave for the imaging. Such techniques include, Synthetic Aperture focusing Technique, Sampled Array Method, Common Source Method, Multi Source Methods, etc.

The invention gives the freedom of usage of array as the arrays can be made from any transduction technologies including piezo-electric, piezo polymer, electromagnetic (Lorentz force and/or magnetostriction), laser, microwaves, oscillators, etc.

It is very obvious that the invention has a very high industrial application and industrial utility due to its simplicity, being more accurate in measurements, and having reduced error thereby having a low level of error prone method and device thereby enabling an efficient, quick and easy analysis of the defects/anomalies in objects/media or specific material properties of an object/media or both.

The method and associated devices described herein is for understanding and illustrative purposes only. The present invention presents a solution to the problems suffered in prior art with single element by creating a novel design of phased array transceiver of virtual sources. An attempt has been made to show few embodiments of methods and devices for easy understanding. The other objects and features of the present invention will become apparent from the following detailed description considered in conjunction with the accompanying drawings. It is to be understood however that embodiments, examples and drawings are designed and explained solely for purposes of illustration and not as a definition of the limits of the invention, for which reference should be made to the appended claims. The description and illustrations have put forth novel features of the invention and it shall be understood that various omissions and substitutions and changes in the form and details of the devices illustrated, and in their operation, may be made by those skilled in the art without departing from the spirit of the invention.

The invention claimed is:

1. A method for detecting defects/anomalies, measuring and evaluating defects/anomalies in an object/media and/or specific material property of an object/media using a phased array wave technique comprising:
   a. dividing a phased array transceiver source into a plurality of virtual sources wherein at least one of the virtual sources is characterized in creating a single virtual beam by arranging a plurality of elements in each virtual source sequentially but without phasing for excitation and each element receiving one pulse and the plurality of elements together creating a plurality of beams having same phase and amplitude thereby virtually creating a single beam having a specific angle and focused at a specific depth,
   b. transmitting and receiving one or more wave signals via the plurality of virtual sources in a controlled manner onto an area to be inspected with a control unit that controls the phased array transceiver source,
   b1. measuring received one or more wave signals, and
   c. evaluating with the control unit the defects/anomalies and/or specific material property on the inspected area by manipulation of the measured one or more wave signals of the plurality of virtual sources.

2. The method as claimed in claim 1, wherein the said one or more wave signals may be an acoustic, ultrasonic, electromagnetic, light, radar and microwave.

3. The method as claimed in claim 1, wherein the said phased array transceiver source may be made from piezo electric, piezo polymer, electromagnetic, laser, micro-waves and oscillator transduction technology.

4. The method as claimed in claim 1, wherein each of the one or more wave signals has a wave mode, the said wave mode may be longitudinal, transverse and guided Rayleigh, Lamb, cylindrical, circumferential, axial, flexural, SH, SV or combination thereof.

5. The method as claimed in claim 1, wherein the control unit further utilizes algorithm using technique including synthetic aperture focusing technique, sampled array method, a common source method, multi-source method or any combination thereof.

6. The method as claimed in claim 1, wherein a configuration of the virtual sources may be two dimensions or three dimensions.

7. The method as claimed in claim 1, wherein the virtual sources generated by the phased array transceiver source are characterized in that a physical location of the said virtual sources may be different from the said phased array transceiver source.

8. The method as claimed in claim 7, wherein a configuration of the virtual sources may be different from a configuration of the said phased array transceiver source.

9. The method as claimed in claim 1, wherein an angle of focusing is based on a geometry of the area to be inspected and thereby a geometry of the volume to be imaged.

10. The method as claimed in claim 1, wherein the defects include anomalies and/or objects include media.

11. A defect/anomaly identification device for identifying, measuring and evaluating defects/anomalies in an object/media and/or identifying, measuring and evaluating specific material property of the object/media comprising:
   a. a phased array transceiver source for use in a phased array wave technique for transmitting and receiving wave signals on and from an area to be inspected wherein the phased array transceiver source is divided into a plurality of virtual sources wherein at least one of the virtual sources is characterized in that the virtual source comprises a plurality of elements arranged sequentially but without phasing for excitation, such that each element of the virtual source receiving one pulse and the plurality of elements together creating plurality of beams having same phase and amplitude, thereby creating a single virtual beam having a specific angle and focused at a specific depth, and
   b. a control unit which controls the phased array transceiver source such that the plurality of the virtual sources each transmitting and receiving a wave signal directly onto and from the area of the object to be inspected, the wave signal being measured, and wherein the control unit directs a plurality of the wave signals onto the area to be inspected, and evaluates the defects/anomalies by manipulation of the measured wave signals of the plurality of virtual sources.

12. The device as claimed in claim 11, wherein the said wave signal may be an acoustic, ultrasonic, electromagnetic, light, radar and microwave.

13. The device as claimed in claim 11, wherein the said phased array transceiver source may be made from piezo electric, piezo polymer, electromagnetic, laser, micro waves and oscillator transduction technology.

14. The device as claimed in claim 11, wherein each of the one or more wave signals has a wave mode, the said wave mode may be longitudinal, transverse and guided Rayleigh, Lamb, cylindrical, circumferential, axial, flexural, SH, SV or combination thereof.

15. The device as claimed in claim 11, wherein the control unit further utilizes algorithm using technique including synthetic aperture focusing technique, sampled array method, a common source method, multisource method or any combination thereof.

16. The device as claimed in claim 11, wherein a configuration of the virtual sources may be two dimension or three dimension.

17. The device as claimed in claim 11, wherein the virtual sources generated by the phased array transceiver source is characterized in that a physical location of the said virtual sources may be different from the said phased array transceiver source.

18. The device as claimed in claim 17 wherein a configuration of the virtual sources may be different from a configuration of the said phased array transceiver source.

19. The device as claimed in claim 11, wherein an angle of focusing is based on a geometry of the area to be inspected and thereby a geometry of the volume to be imaged.

20. The method as claimed in claim 11, wherein the defects include anomalies and/or objects include media.

* * * * *